(12) United States Patent
Lin et al.

(10) Patent No.: US 8,892,202 B2
(45) Date of Patent: Nov. 18, 2014

(54) CURRENT STIMULATOR

(75) Inventors: Chun-Yu Lin, Hualien County (TW); Yi-Ju Li, Taichung (TW); Ming-Dou Ker, Hsinchu County (TW)

(73) Assignee: National Chiao Tung University, Hsinchu (TW)

( * ) Notice: Subject to any disclaimer, the term of this patent is extended or adjusted under 35 U.S.C. 154(b) by 289 days.

(21) Appl. No.: 13/439,365

(22) Filed: Apr. 4, 2012

(65) Prior Publication Data

US 2013/0172958 A1    Jul. 4, 2013

(30) Foreign Application Priority Data

Dec. 30, 2011    (TW) .............................. 100149927 A

(51) Int. Cl.
*A61N 1/08*    (2006.01)
*A61N 1/18*    (2006.01)

(52) U.S. Cl.
USPC .............................................. 607/5; 607/34

(58) Field of Classification Search
CPC ........... A61N 1/36153; A61N 1/36157; A61N 1/3782; A61N 1/3981
USPC .......................................................... 607/34
See application file for complete search history.

(56) References Cited

U.S. PATENT DOCUMENTS

| | | | |
|---|---|---|---|
| 5,372,605 A * | 12/1994 | Adams et al. ...................... | 607/5 |
| 6,289,246 B1 | 9/2001 | Money | |
| 7,881,803 B2 | 2/2011 | Parramon et al. | |
| 2005/0131496 A1 * | 6/2005 | Parramon et al. ............... | 607/61 |
| 2005/0259454 A1 * | 11/2005 | Varrichio et al. ............... | 363/61 |
| 2010/0211132 A1 * | 8/2010 | Nimmagadda et al. ......... | 607/60 |

FOREIGN PATENT DOCUMENTS

TW    I329027    8/2010

OTHER PUBLICATIONS

W. Stacey et al., "Technology insight: neuroengineering and epilepsy—designing devices for seizure control," *Nature Clinical Practice Neurology*, vol. 4, No. 4, pp. 190-201, Apr. 2008.
C. Young et al., "A portable wireless online closed-loop seizure controller in freely moving rats," *IEEE Transactions on Instrumentation and Measurement*, vol. 60, No. 2, pp. 513-521, Feb. 2011.
W.L. Chen et al., "Design of stimulus driver to suppress epileptic seizure with adaptive loading consideration," in *Proc. IEEE International Symposium on Next-Generation Electronics*, 2010, pp. 9-12.
B. Serneels et al., "A high-voltage output driver in a 2.5-V 0.25-μm CMOS technology," *IEEE Journal of Solid-State Circuits*, vol. 40, No. 3, pp. 576-583, Mar. 2005.
S. Kelly et al., "A power-efficient neural tissure stimulator with energy recovery," *IEEE Transactions on Biomedical Circuits and Systems*, vol. 5, No. 1, pp. 20-29, Feb. 2011.

* cited by examiner

*Primary Examiner* — Christopher D Koharski
*Assistant Examiner* — Natasha Patel
(74) *Attorney, Agent, or Firm* — Muncy, Geissler, Olds & Lowe, P.C.

(57) ABSTRACT

The disclosure relates to a current stimulator, which comprises a high voltage output module, a voltage control module and a charge pump module. The high voltage output module includes a plurality of stacked transistors, and receives an input control signal able to turn on/off the current stimulator and a first voltage. A second voltage is generated by adding the voltages output by all the transistors to the first voltage and then output to the voltage control module. The voltage control module outputs a voltage control signal able to stabilize the stimulus current for the load according to the second voltage and the load impedance variation. The charge pump regulates the first voltage according to the voltage control signal, and outputs the regulated first voltage to the high voltage output module. Thereby, the current stimulator can adaptively stabilize the stimulus current, responding to load impedance variation.

9 Claims, 3 Drawing Sheets

CURRENT STIMULATOR

BACKGROUND OF THE INVENTION

1. Field of the Invention

The present invention relates to a current stimulator, particularly to a load-adaptive current stimulator fabricated in a low voltage IC process and able to output a stimulus voltage much higher than the supply voltage.

2. Description of the Related Art

Wafer foundries are flourishing in Taiwan. Without having to go far, IC industry of Taiwan is supported by the neighboring world-class wafer foundries and is growing fast with high technical burst power. IC industry of Taiwan has successfully developed various IC products. Further, the related organizations and manufacturers also integrate IC technology with biological technology to improve the medical environment and promote health of people.

Electric stimulus is an emerging medical technology and regarded as an alternative route to cure some illnesses thought incurable before, wherein current is used to stimulate a region to restore the function thereof. Advance in IC miniaturization makes it feasible to incorporate an intelligent bionic system in a single chip. Although different types of circuits can be integrated in a system-on-chip (SOC), there is still a problem for SOC current stimulators: current stimulators have to operate in a high voltage environment. When an IC fabricated in low voltage IC process operates in a high voltage environment, the voltage may be greater than the withstand voltage of the elements. In such a case, IC is likely to have problems of electric overstress, low gate-oxide reliability, hot-carrier degradation, and leakage current.

Besides, the load impedance varies with the region where the current stimulator is attached. Even in the case that the current stimulator is applied to the same region, the load impedance may vary with the materials of the electrodes and the duration of applying current stimulation. When the load impedance does not match, the stimulus current is no more effectively output.

Accordingly, the present invention proposes a current stimulator to overcome the abovementioned problems.

SUMMARY OF THE INVENTION

The primary objective of the present invention is to provide a current stimulator, wherein the elements fabricated with a low voltage IC process are used to generate high voltage, whereby is overcome the problem of electric overstress.

Another objective of the present invention is to provide a current stimulator, which can maintain the value of stimulus current when the load impedance varies, whereby is delivered a stable stimulus current and promoted safety and reliability.

To achieve the abovementioned objectives, the present invention proposes a current stimulator, which comprises a high voltage output module, a voltage control module, and a charge pump module. The high voltage output module is electrically connected with the voltage control module. The high voltage output module includes a plurality of transistors stacked together. The high voltage output module receives an input control signal able to turn on/off the current stimulator and a first voltage. The voltages output by all the transistors are added to the low-level first voltage to form a high-level second voltage. The second voltage is output to the voltage control module. Thereby, the present invention can use the low-voltage elements to generate high voltage. The voltage control module is electrically connected with the high voltage output module. As the load impedance may vary dramatically, the voltage control module outputs a voltage control signal able to stabilize the stimulus current for the load according to the second voltage and the variation of load impedance. The charge pump is electrically connected with the voltage control module and the high voltage output module. The charge pump receives the voltage control signal, regulates the first voltage, and outputs the regulated first voltage to the high voltage output module. Thereby, the current stimulator of the present invention can adaptively stabilize the stimulus current, confronting the variation of the load impedance.

Below, the embodiments are described in detail to make easily understood the objectives, technical contents, characteristics and accomplishments of the present invention.

DETAILED DESCRIPTION OF THE INVENTION

The present invention proposes a current stimulator, which can integrate with other circuits to form a single chip that can be implanted into an animal body to provide current stimulation therapy. Considering safety, reliability and power consumption, the present invention adopts a low voltage IC process to fabricate a current stimulator, whereby are solved the problems of electric overstress, low gate-oxide reliability, hot-carrier degradation, and leakage current that occur in the conventional current stimulator operating in a high voltage environment.

Figure 1:
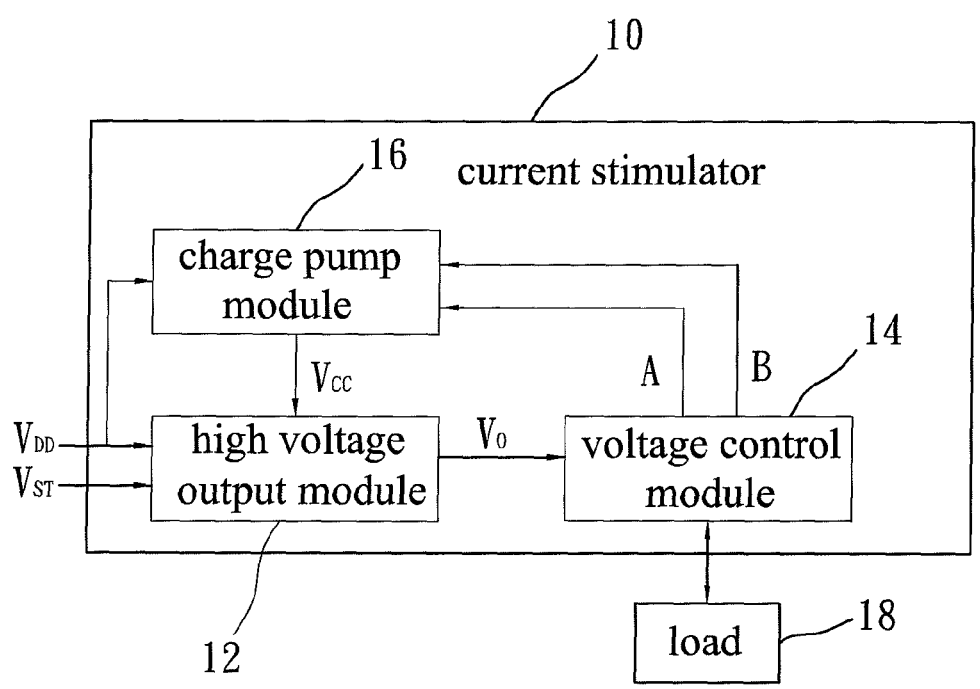
FIG. 1 schematically shows the structure of a current stimulator according to one embodiment of the present invention.

Refer to FIG. 1 schematically showing the structure of a current stimulator according to one embodiment of the present invention. The current stimulator 10 of the present invention comprises a high voltage output module 12, a voltage control module 14 and a charge pump module 16. The high voltage output module 12 is electrically connected with the voltage control module 14 and the charge pump module 16. The high voltage output module 12 includes a plurality of transistors stacked together. It should be noted that the present invention uses a transistor configuration design to increase the withstand voltage by N times (the detail will be described thereinafter). The on/off of the current stimulator 10 is controlled by an input control signal ($V_{ST}$). When the high voltage output module 12 receives an input control signal for starting the current stimulator 10, a power supply module provides a supply voltage $V_{DD}$ for the high voltage output module 12 to start the operation of the high voltage output module 12. At beginning, the high voltage output module 12 receives a first voltage $V_{CC}$ from the charge pump 16. The low-level first voltage $V_{CC}$ is stepped up into a high-level second voltage $V_O$ by the stacked transistors. The second voltage $V_O$ is output to the voltage control module 14. As the impedance of a load 18 (the region to be stimulated) varies dramatically, the voltage control module 14 detects the variation of the impedance of the load 18 in advance to determine the value of a stimulus current. The voltage control module 14 also outputs a voltage control signal A and a voltage control signal B according to the second voltage and the variation of the load impedance. The charge pump 16 receives the voltage control signals and supplies an appropriate value of the first voltage to the high voltage output module 12. Thereby, the current stimulator 10 of the present invention can adapt itself to stabilize the output current.

Figure 2:
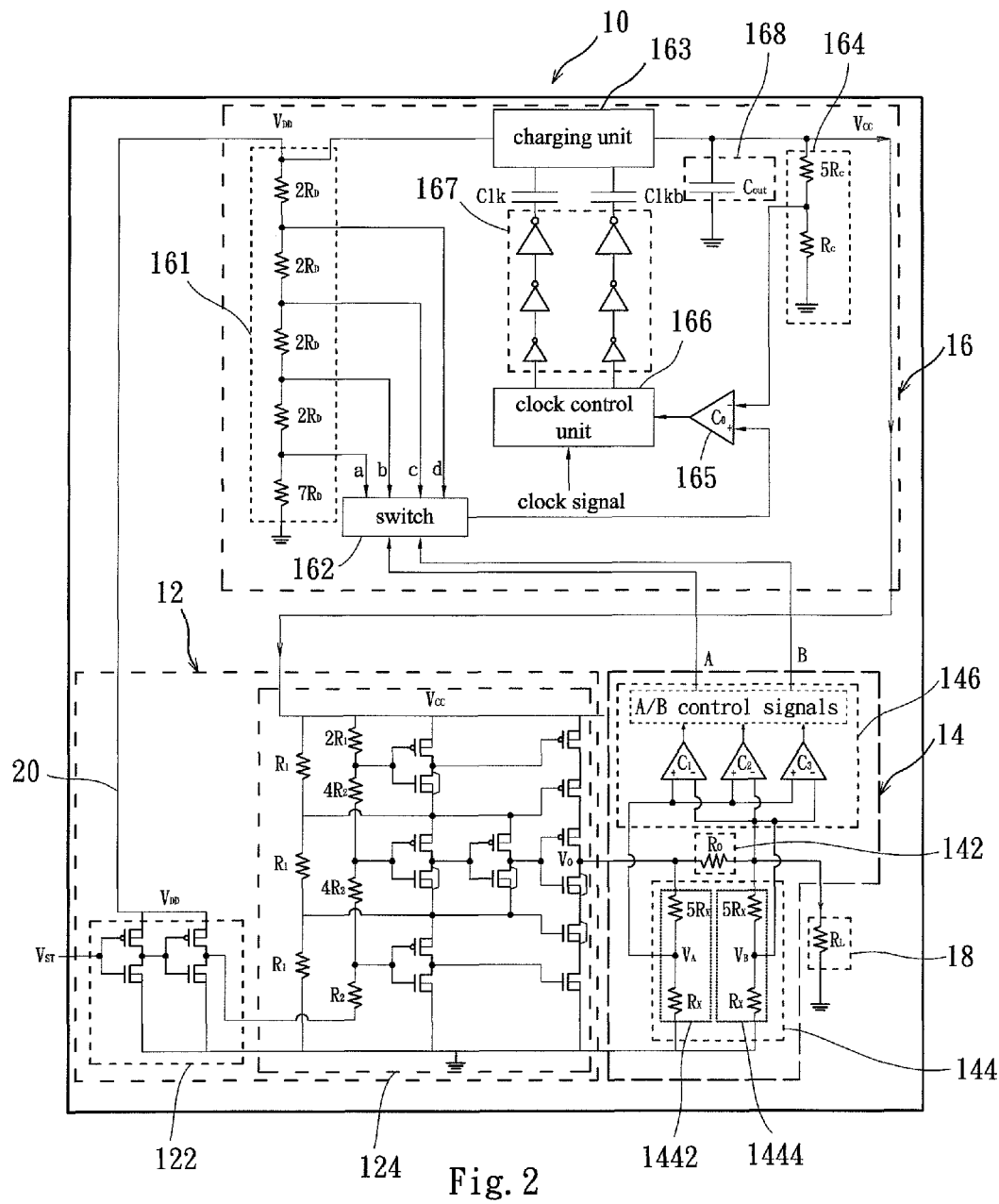
FIG. 2 shows the detailed circuit of a current stimulator according to one embodiment of the present invention.

Below are explained in detail the reason why the present invention can use the elements fabricated in a low voltage IC process to generate high voltage and the reason why the current stimulator 10 can stabilize the output current when the load impedance varies within specified ranges. Refer to FIG. 2 showing the detailed circuit of a current stimulator according to one embodiment of the present invention. The high voltage output module 12 includes a driving unit 122 and a high voltage output unit 124. The high voltage output unit 124 has a plurality of first voltage division resistors ($R_1$) and a plurality of second voltage division resistors ($R_2$) and a plurality of transistors connected with the voltage division resistors, wherein the voltage division resistors are connected in series. The driving unit 122 receives the input control signal VST and the supply voltage $V_{DD}$ provided by a power supply module 20 and drives the high voltage output unit 124 to operate. The cascade second voltage resistors $R_2$ receive the supply voltage. The power supply module is a low voltage element and outputs a low-level supply voltage, such as a voltage of 1.8-3.3V. The cascade second voltage division resistors $R_2$ convert the low-level supply voltage into a high-level voltage and output the high-level voltage to drive the transistors. The high-level first voltage $V_{CC}$ is divided by the cascade first voltage division resistors $R_1$. The divided voltage are respectively supplied to drive the rear-end transistors. As the voltage drop between each two terminals of each transistor is lower than 3.3V (the voltage the transistor can withstand for 0.18 μs), the present invention is exempted from the problems of electric overstress, poor gate-oxide reliability, hot-carrier degradation and leakage current. The output voltages of all the transistors are added to the first voltage to generate the high-level second voltage $V_O$. Then, the high-level second voltage is output to the voltage control module 14.

The voltage control module 14 includes an output impedance unit 142, a first voltage division unit 144 and at least one voltage comparator 146, which are electrically connected. The output impedance unit 142 is an output resistor ($R_O$) arranged between the voltage output terminal of the high voltage output module 12 and the load ($R_L$) 18. The output impedance unit 142 receives the second voltage, converts the second voltage into a stimulus current and then outputs the stimulus current to the load 18. The terminal voltage (voltage drop) of the output impedance unit 142 is varied according to the variation of the impedance of the load 18. Therefore, the voltage comparator 146 can estimate the value of the stimulus current according to the terminal voltage of the output impedance unit 142. Note that the voltage comparator 146 is a low-voltage element and that what is received by the output impedance unit 142 is the high-level second voltage. In order that the rear-end voltage comparator 146 can operate stably, the first voltage division unit 144 divides the high-level voltage and outputs the divisional voltage to the voltage comparator 146.

The first voltage division unit 144 has a first voltage division sub-unit 1442 and a second voltage division sub-unit 1444. The output terminals of the first voltage division sub-unit 1442 and the second voltage division sub-unit 1444 are connected with the voltage comparator 146. The first voltage division sub-unit 1442, such as the cascaded resistors $5R_X$ and $R_X$, are connected with the voltage output terminal of the high voltage output module 12 and the output impedance unit 142. The first voltage division sub-unit 1442 performs voltage division according to the voltage drop between the voltage output terminal of the high voltage output module 12 and the output impedance unit 142 to generate a third voltage ($V_A$). The second voltage division sub-unit 1444, such as the cascaded resistors $5R_X$ and $R_X$, is connected with the output impedance unit 142 and the load 18 and performs voltage division according to the voltage drop between the output impedance unit 142 and the load 18 to generate a fourth voltage ($V_B$). Then, the voltage comparator 146 compares the third voltage and the fourth voltage to determine the value of the stimulus current and output voltage control signals A and B to the charge pump 16.

In order that the current stimulator 10 can provide stable stimulus current for the load 18 when the impedance of the load 18 varies, the impedance of the load 18 are divided into four ranges in one embodiment, including 100-133 kΩ, 133-168 kΩ, 168-213 kΩ, and 213-250 kΩ. In one embodiment, there are three voltage comparators $C_1$, $C_2$ and $C_3$. The third voltage and the fourth voltage are respectively allocated to the voltage comparators according to the voltage levels thereof. The voltage comparators perform comparison and outputs voltage control signals, such as Signals 00, 01, 11 and 10. When the size of each range is decreased, the number of the ranges increases. In such a case, the number of the voltage comparators is increased correspondingly, and the voltage control signals become more accurate.

The charge pump 16 includes a second voltage division unit 161, a switch 162, a charging unit 163, a voltage feedback unit 164, a voltage output comparator 165, and a clock control unit 166. The second voltage division unit 161 is connected with a voltage supply module (not shown in the drawings) and receives a supply voltage ($V_{DD}$) from the voltage supply module. The second voltage division unit 161 has a plurality of voltage division resistors ($R_D$) respectively outputting different levels of divisional voltages. The second voltage division unit 161 is connected with the switch 162, and the voltage control signals determine the levels of divisional voltages. In other words, the switch 162 selects one of the divisional voltage levels from the second voltage division unit 161 according to the voltage control signal and outputs the selected divisional voltage level. For example, the switch 162 selects a divisional voltage level a for a voltage control signal 00, a divisional voltage level b for a voltage control signal 01, a divisional voltage level c for a voltage control signal 11, a divisional voltage level d for a voltage control signal 10. Suppose the voltage control signal is 00. The switch 162 inputs the divisional voltage level a to the positive electrode ($V^+$) of the voltage output comparator ($C_O$) 165. The voltage feedback unit 164 feeds back the first voltage ($V_{CC}$) as a feedback voltage to the negative electrode ($V^-$) of the voltage output comparator ($C_O$) 165. The voltage output comparator 165 compares the divisional voltage level a with the feedback voltage. If the feedback voltage is greater than or equal to the divisional voltage level a, the voltage output comparator 165 outputs a comparison control signal to the clock control unit 166. According to the comparison control signal and a clock signal, the clock control unit 166 controls the charging unit 163 to stop charging. If the feedback voltage is smaller than the divisional voltage level a, the clock control unit 166 controls the charging unit 163 to start charging. A voltage buffer unit 167 may be interposed between the clock control unit 166 and the charging unit 163 to modify the charging state of the charging unit 163. Besides, a capacitor ($C_{out}$) 168 may be interposed between the charging unit 163 and the voltage feedback unit 164 to store the charging voltage of the charging unit 163 and prevent the charging voltage from being instantaneously transmitted to the high voltage output module 12, whereby the entire circuit can operate more stably.

Further, the charge pump 16 regulates the first voltage ($V_{CC}$) supplied to the high voltage output module 12 so that the voltage control module 14 can adaptively output a stable stimulus current, responding to the impedance variation of the load 18.

Figure 3A:
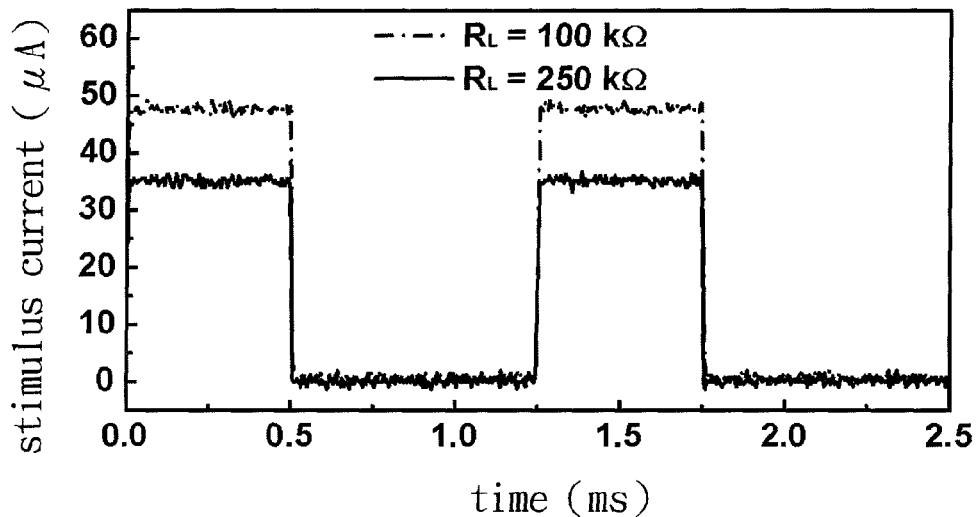
FIG. 3A and FIG. 3B show the waveforms obtained in the simulation of the application of the present invention to a living body.
Figure 3B:
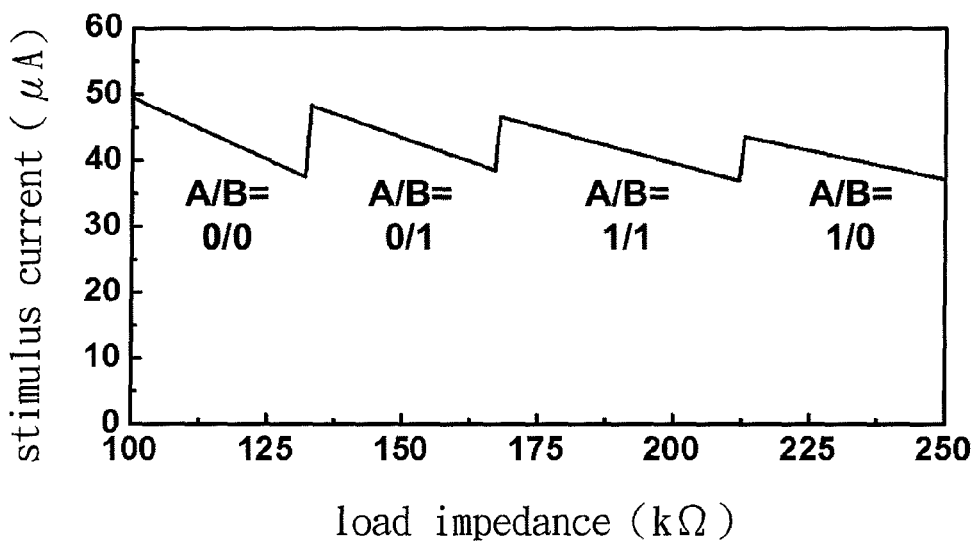

When the present invention is applied to an epilepsy-inhibiting device, the variation of the nidus tissue will change the impedance of the load 18 (the stimulated region). Refer to FIG. 3A and FIG. 3B showing the waveforms obtained in the simulation of the application of the present invention to a living body. In one embodiment, the impedance of the load 18 is divided into four ranges, and three voltage comparators are used to respectively output the voltage control signals corresponding to the four ranges of load impedance. As shown in FIG. 3A, the load impedance varies from 100-250 k$\Omega$, needing a stimulus current ranging from 30 to 50 μA. As shown in FIG. 3B, the voltage control signal is varied to generate the required stimulus current according to the impedance variation of the load.

In conclusion, the current stimulator can indeed output stable stimulus current when the load impedance varies within specified ranges. Further, the present invention uses low voltage elements to achieve high voltage output, whereby is overcome the problem of electric overstress occurring in the conventional technology and promoted safety and reliability of current stimulators.

The embodiments described above are only to exemplify the present invention but not to limit the scope of the present invention. Any equivalent modification or variation according to the characteristic or spirit of the present invention is to be also included within the scope of the present invention.

What is claimed is:

1. A current stimulator comprising:
   a high voltage output module including a plurality of transistors stacked together, receiving an input control signal and a first voltage, wherein voltages output by all said transistors are added to said first voltage to form a second voltage;
   a voltage control module electrically connected with said high voltage output module and outputting a voltage control signal for providing a stable stimulus current for a load according to said second voltage and variation of impedance of said load; and
   a charge pump module electrically connected with said high voltage output module and said voltage control module, receiving said voltage control signal, and regulating said first voltage supplied to said high voltage output module;
   wherein said charge pump module further comprises a second voltage division unit, a switch, a charging unit, a voltage feedback unit, a voltage output comparator and a clock control unit, and wherein said second voltage division unit is connected with a voltage supply module and receives a supply voltage from said voltage supply module, and wherein said switch selects one of divisional voltage levels of said second voltage division unit as a selected divisional voltage level according to said voltage control signal and outputs said selected divisional voltage level to said voltage output comparator, and wherein said voltage feedback unit feeds back said first voltage as a feedback voltage to said voltage output comparator, and wherein said voltage output comparator compares said feedback voltage and said selected divisional voltage level and outputs a comparison control signal to said clock control unit, and wherein said clock control unit controls said charging unit to operate according to said comparison control signal and a clock signal.

2. The current stimulator according to claim 1, wherein said high voltage output module further comprises a driving unit and a high voltage output unit, which are electrically connected, and wherein said high voltage output unit includes a plurality of voltage division resistors and said transistors connected with said voltage division resistors, and wherein said driving unit receives said input control signal and then drives said high voltage output unit to transform said first voltage into said second voltage.

3. The current stimulator according to claim 2, wherein said driving unit receives a supply voltage from a power supply module.

4. The current stimulator according to claim 1, wherein said voltage control module further comprises an output impedance unit, a first voltage division unit and at least one voltage comparator, which are electrically connected, and wherein said output impedance unit receives said second voltage and varies a terminal voltage thereof according to an impedance of said load, and wherein said first voltage division unit performs voltage division and generates a third voltage and a fourth voltage, and wherein said voltage comparator compares said third voltage and said fourth voltage and generates said voltage control signal.

5. The current stimulator according to claim 4, wherein said output impedance unit is an output resistor connected with said high voltage output module and said load, and wherein said output impedance unit transforms said second voltage into a stimulus current and outputs said stimulus current to said load.

6. The current stimulator according to claim 4, wherein said voltage control module has a plurality of voltage comparators, and wherein said third voltage and said fourth voltage are allocated to said voltage comparators according to voltage levels thereof, and wherein said voltage comparators output said voltage control signals after comparison.

7. The current stimulator according to claim 4, wherein said first voltage division unit includes a first voltage division sub-unit and a second voltage division sub-unit, and wherein voltage output terminals of said first voltage division sub-unit and said second voltage division sub-unit are connected with said voltage comparator.

8. The current stimulator according to claim 1, wherein said second voltage division unit includes a plurality of voltage division resistors respectively outputting different divisional voltage levels and connected with said switch, and wherein said voltage control signal selects one of said divisional voltage levels as said selected divisional voltage level, and wherein said switch inputs said selected divisional voltage level to said voltage output comparator.

9. The current stimulator according to claim 1, wherein when said feedback voltage is greater than or equal to said selected divisional voltage level, said clock control unit controls said charging unit to stop charging, and wherein when said feedback voltage is smaller than said selected divisional voltage level, said clock control unit controls said charging unit to start charging.

* * * * *